United States Patent
Matsuzawa et al.

(10) Patent No.: US 10,492,487 B2
(45) Date of Patent: *Dec. 3, 2019

(54) VITRIFICATION-CRYOPRESERVATION IMPLEMENT FOR CELLS OR TISSUES

(71) Applicant: MITSUBISHI PAPER MILLS LIMITED, Tokyo (JP)

(72) Inventors: Atsushi Matsuzawa, Tokyo (JP); Katsumitsu Susaki, Tokyo (JP)

(73) Assignee: MITSUBISHI PAPER MILLS LIMITED, Tokyo (JP)

( * ) Notice: Subject to any disclaimer, the term of this patent is extended or adjusted under 35 U.S.C. 154(b) by 430 days.

This patent is subject to a terminal disclaimer.

(21) Appl. No.: 14/785,331

(22) PCT Filed: May 14, 2014

(86) PCT No.: PCT/JP2014/062862
§ 371 (c)(1),
(2) Date: Oct. 17, 2015

(87) PCT Pub. No.: WO2014/185457
PCT Pub. Date: Nov. 20, 2014

(65) Prior Publication Data
US 2016/0057991 A1    Mar. 3, 2016

(30) Foreign Application Priority Data

May 16, 2013 (JP) ................. 2013-103944
Jun. 19, 2013 (JP) ................. 2013-128265
Mar. 28, 2014 (JP) ................. 2014-069296

(51) Int. Cl.
*A01N 1/02*    (2006.01)

(52) U.S. Cl.
CPC ........... *A01N 1/0242* (2013.01); *A01N 1/021* (2013.01); *A01N 1/0268* (2013.01)

(58) Field of Classification Search
CPC .................................................. A01N 1/0268
See application file for complete search history.

(56) References Cited

U.S. PATENT DOCUMENTS 4,245,744 A * 1/1981 Daniels .................. D04H 1/64
                                                    206/210
5,981,044 A * 11/1999 Phan ..................... D21H 17/06
                                                    162/127
(Continued)

FOREIGN PATENT DOCUMENTS

JP    H03-289955 A    12/1991
JP    H05-176946 A    7/1993
(Continued)

OTHER PUBLICATIONS

The International Bureau of WIPO, "International Preliminary Report on Patentability," issued in International Application No. PCT/JP2014/062862, of which U.S. Appl. No. 14/785,331 is a U.S. national phase entry, dated Aug. 5, 2014, 11 pages (7 pages of English Translations and 4 pages of International Preliminary Report on Patentability).

(Continued)

*Primary Examiner* — Jonathan M Hurst

(57) ABSTRACT

The present invention relates to a jig for vitrification cryopreservation of cell or tissue, having a metallic support, and a vitrification solution absorber including an adhesion layer and a vitrification solution-absorbing layer on the metallic support in the order from the side closer to the metallic support.

16 Claims, 3 Drawing Sheets

(56) References Cited

U.S. PATENT DOCUMENTS

| | | | |
|---|---|---|---|
| 6,145,504 A | 11/2000 | Miyake | |
| 6,638,755 B1 | 10/2003 | Mizouchi et al. | |
| 9,516,876 B2 * | 12/2016 | Inoue | G01N 1/42 |
| 2001/0039406 A1 | 11/2001 | Hamajima et al. | |
| 2004/0235182 A1 | 11/2004 | Jones | |
| 2009/0221047 A1 | 9/2009 | Schindler et al. | |
| 2010/0151174 A1 * | 6/2010 | Graff | B32B 15/12 428/43 |
| 2017/0135335 A1 * | 5/2017 | Matsuzawa | A01N 1/0252 |

FOREIGN PATENT DOCUMENTS

| | | |
|---|---|---|
| JP | H07-289235 A | 11/1995 |
| JP | H10-121021 A | 5/1998 |
| JP | H10-248860 A | 9/1998 |
| JP | 2000-000251 A | 1/2000 |
| JP | 3044323 B1 | 3/2000 |
| JP | 2000-212532 A | 8/2000 |
| JP | 2000-325072 A | 11/2000 |
| JP | 2002-315573 A | 10/2002 |
| JP | 2005-040073 A | 2/2005 |
| JP | 2006-521823 A | 9/2006 |
| JP | 2006-271395 A | 10/2006 |
| JP | 2008-222640 A | 9/2008 |
| JP | 2009-526527 A | 7/2009 |
| JP | 2009-240816 A | 10/2009 |
| JP | 5278978 B2 | 5/2013 |
| WO | 2011/070973 A1 | 6/2011 |
| WO | WO 2013/051521 * 4/2013 | C12M 1/00 |

OTHER PUBLICATIONS

Akira Sakai, "Cryopreservation of Cultured Plant Cells and Meristems by Vitrification", Cryobiology and Cryotechnology, vol. 42, No. 1, pp. 61-68 (1996).

P. L. Steponkus et al., "Cryopreservation of *Drosophila melanogaster* embryos", Nature, vol. 345, pp. 170-172 (May 10, 1990).

* cited by examiner

VITRIFICATION-CRYOPRESERVATION IMPLEMENT FOR CELLS OR TISSUES

CROSS REFERENCE TO RELATED APPLICATIONS

This patent application is a U.S. national stage application under 35 U.S.C. § 371 of International Patent Application No. PCT/JP2014/062862 filed on May 14, 2014, which claims the benefit of foreign priority to Japanese Patent Application Nos. JP 2013-103944 filed on May 16, 2013, JP 2013-128265 filed on Jun. 19, 2013, and JP 2014-069296 filed on Mar. 28, 2014. The International Application was published in Japanese on Nov. 20, 2014, as International Publication No. WO 2014/185457 A1 under PCT Article 21(2).

FIELD OF THE INVENTION

The present invention relates to a jig for vitrification cryopreservation to be used when a biological cell or tissue etc. is to be cryopreserved.

BACKGROUND ART

In various industrial fields, researchers have studied to develop more sophisticated preservation technology for biological cells or tissues. For example, in bovine embryo transplantation technology, an embryo is transplanted corresponding to the estrous cycle of the recipient cattle of the embryo. In order to carry out the embryo transplantation, the embryo is generally cryopreserved and then is thawed for the transplantation corresponding to the estrous cycle. In the infertility treatment of human, after an ovum or ovary is collected from a mother, it is cryopreserved and then is thawed upon the transplantation to use.

Generally, even though in a culture solution, long term culture of a cell or tissue placed outside a living body is undesirable since the cell or tissue collected from the living body gradually loses its biological activity. Therefore, it is very important to develop technology for long-term preservation of the cell without losing its biological activity. The development of the technology is expected to allow the collected cell or tissue to be analyzed with high accuracy and used for transplantation while keeping its higher biological activity, which results in the improvement of engraftment rate after the transplantation. In addition, the development of the technology is also expected to allow a skin cultured in vitro or an artificial tissue constructed in vitro, such as what is called cell sheet, to be sequentially produced and preserved for use when necessary. Thus, the development of the technology is expected to bring us significant advantages in terms of industries as well as medical treatment.

As a preservation method for cell or tissue, for example, the slow freezing method has been known. The first step of this method is to immerse a cell or tissue in a preservation solution obtained by incorporating a cryoprotectant into a physiological solution such as phosphate buffered saline. As a cryoprotectant, some compounds such as glycerol, ethylene glycol are used. After immersing the cell or tissue in the preservative solution, cooling it to −30 to −35° C. at a relatively slow cooling rate (e.g., speed of 0.3 to 0.5° C./min.) provides a sufficient refrigeration and a high viscosity for the solutions inside and outside of the cell or tissue. In such a state, further cooling to the temperature of liquid nitrogen (−196° C.) for the cell or tissue in the preservation solution causes the vitrification phenomenon in which a very small amount of solutions existing inside of the cell or tissue and around outside thereof both turn solid while remaining non-crystalline. Since the solidification inside and outside the cell or tissue by vitrification makes the movement of the molecules therein substantially stop, the cell or tissue vitrified in liquid nitrogen would be preserved semi-permanently.

However, since the slow freezing method mentioned above requires cooling at a relatively low cooling rate, it takes time to carry out the cryopreservation. Also, there is a problem that the method requires a device or jig for controlling temperature. In addition, since the slow freezing method forms ice crystals in the preservation solution outside the cell or tissue, the cell or tissue may suffer physical damage from the ice crystals.

As a method for solving the problems in the slow freezing method, a vitrification preservation method has been proposed. The vitrification preservation method applies the principle that ice crystals are hardly produced even below zero by cryoscopy of a solution containing a large amount of cryoprotectant such as glycerol, ethylene glycol, or DMSO (dimethyl sulfoxide). Rapid refrigeration of this solution in liquid nitrogen can bring solidification while not making ice crystals. Such solidification is called vitrification congelation. Also, the solution containing a large amount of cryoprotectant is called vitrification solution.

A specific handling of the vitrification method is to immerse a cell or tissue in the vitrification solution and then to freeze it at the temperature of liquid nitrogen (−196° C.) Since the vitrification method is such a simple and rapid process, it has some advantages that there is no need to take time to carryout the cryopreservation, and no need for a device or jig for controlling temperature.

With the vitrification method, it is possible to avoid physical damage (frost damage) to the cell during freezing and during thawing for not producing ice crystals inside nor outside of the cell. On the other hand, the cryoprotectant of high concentration in the vitrification solution has chemical toxicity. Thus, it is preferable for the vitrification solution existing around the cell or tissue during cryopreservation to be less, and for the time when the cell is exposed to the vitrification solution, namely the time until the freezing, to be short. Furthermore, there is a need to dilute the vitrification solution immediately after thawing.

Regarding the cryopreservation of a cell or tissue using the vitrification preservation method, examples of various ways using various types of the cell or tissue are illustrated. For example, Patent Document 1 shows that the application of vitrification preservation method to a reproductive or somatic cell of an animal or human is extremely useful in terms of the survival rate after the cryopreservation and thawing.

The vitrification preservation method is a technology developed chiefly using the reproductive cell of human. Nowadays, the application to iPS cell or ES cell is widely investigated. Further, Non-Patent Document 1 shows that the vitrification preservation method was effective in the preservation of *Drosophila* embryo. Furthermore, Non-Patent Document 2 shows that the vitrification preservation method is effective in the preservation of a cultured plant cell and tissue. Thus, the vitrification method is known to be useful for the preservation of a wide variety of species of cell and tissue.

As a jig and an operation method for more efficiently performing the vitrification preservation method, Patent Document 2 and Patent Document 3, etc. illustrate an attempt that is made to improve the regeneration rate of ovum or embryo by performing the vitrification cryopreservation thereof in a straw filled with the vitrification solution and by being quickly contacted with a dilution solution at the time of thawing.

Patent document 4 describes a method that can cryopreserve the reproductive cell of ovum or embryo with high survivability by absorbing the extra vitrification solution attached around it with an absorber such as a filter paper.

Patent Documents 5 and 6 describe what is called Cryotop method, which is used in the infertility treatment field of human. The method uses a tool for ovum cryopreservation with a film of a strip for the ovum adhesion retention which film is flexible and colorless transparent, and makes the ovum or embryo adhere to the film together with a very small amount of the vitrification solution under the microscope to cryopreserve.

Patent Document 7 describes a method of cryopreserving a collected tissue fragment using a plate for tissue fragment cryopreservation, which plate is made of a metallic board-formed material, and has a lot of holes to which a cooling medium can gain entry.

RELATED ARTS

Patent Documents

Patent Document 1: JP-B-3044323
Patent Document 2: JP-A-Hei-5/176946
Patent Document 3: JP-A-Hei-10/248860
Patent Document 4: JP-A-2005/40073
Patent Document 5: JP-A-2002/315573
Patent Document 6: JP-A-2006/271395
Patent Document 7: JP-A-2008/222640

Non-Patent Documents

Non-Patent Document 1: Steponkus et al., Nature 345: 170-172 (1990)
Non-Patent Document 2: Akira Sakai, Journal of JSCC 42: 61-68 (1996)

SUMMARY OF THE INVENTION

Problem to be Solved by the Invention

Patent Document 4 mentioned above describes a process that can cryopreserve a reproductive cell of ovum or embryo with high survivability by absorbing the extra vitrification solution attached around it with an absorber such as a filter paper. However, the method has a problem that a sufficient cooling rate cannot be obtained in the case of vitrification preservation for aggregation of the cells which overlap each other, or for tissue. Also, it is difficult to visually observe the cell or tissue adhering to the absorber under a transmission microscope or a reflection microscope.

The methods described in Patent Document 5 and Patent Document 6 can cryopreserve an ovum or embryo by adhering it dropwise to a colorless transparent flat film together with a very small amount of the vitrification solution. However, in practice, it is very difficult to drop the cell together with a very small amount of the vitrification solution, and it requires a high degree of skill. Further, in the case of using the ovum cryopreservation tool for vitrification cryopreservation of a cell aggregation consisting of a number of cells or a tissue, extra vitrification solution remains around the cell or tissue since the amount thereof attached to the cell or tissue also becomes larger, and the survivability of the cell or tissue may decrease due to the toxicity of the vitrification solution itself. Furthermore, as with the problem in Patent Document 4, the method also has a problem that a sufficient cooling rate cannot be obtained.

The method described in Patent Document 7 makes an improvement for obtaining a rapid cooling rate in the preservation of ovarian tissue by using a metal plate with high thermal conductivity, and further by having a lot of holes into which liquid nitrogen, a cooling medium, can enter. However, as with the problem in Patent Document 5 or Patent Document 6, extra vitrification solution remains around the tissue and the cell organizing the tissue, and the survivability of the tissue and the cell organizing the tissue may decrease due to the toxicity of the vitrification solution.

The present invention mainly aims to provide a jig for vitrification cryopreservation with which the cryopreservation operation for cell or tissue can be performed easily and reliably. More specifically, the present invention mainly aims to provide a jig for vitrification cryopreservation which has an excellent absorption capability of absorbing extra vitrification solution on dropping the vitrification solution together with a cell or tissue, and is capable of holding reliably the cell or tissue even at the time of freezing or at the time of thawing. The present invention further aims to provide a jig for vitrification cryopreservation which is excellent in visibility for cell or tissue under microscopic observation.

Means for Solving Problem

The present inventors have found, as a result of intensive studies to solve the above problems, that the above problems can be solved by a jig for vitrification cryopreservation of cell or tissue having the following constitution (herein, "jig for vitrification cryopreservation of cell or tissue", also referred to simply as "jig for vitrification cryopreservation").

(1) A jig for vitrification cryopreservation of cell or tissue, characterized in having a metallic support, and a vitrification solution absorber including an adhesion layer and a vitrification solution-absorbing layer on the metallic support in the order from the side closer to the metallic support.
(2) The jig for vitrification cryopreservation of cell or tissue according to the above (1), wherein the vitrification solution-absorbing layer is a paper or a nonwoven fabric.
(3) The jig for vitrification cryopreservation of cell or tissue according to the above (2), wherein the basis weight of the vitrification solution-absorbing layer is 20 g/m$^2$ or more.
(4) The jig for vitrification cryopreservation of cell or tissue according to the above (2), wherein the density of the vitrification solution-absorbing layer is 0.25 g/cm$^3$ or less.
(5) The jig for vitrification cryopreservation of cell or tissue according to the above (2), wherein the density of the vitrification solution-absorbing layer is 0.5 g/cm$^3$ or less and the basis weight is 100 g/m$^2$ or less.
(6) The jig for vitrification cryopreservation of cell or tissue according to any one of the above (2) to (4), wherein the vitrification solution-absorbing layer has a fiber of 4 μm or less in average fiber diameter.
(7) The jig for vitrification cryopreservation of cell or tissue according to any one of the above (1) to (6), wherein the adhesion layer contains at least one of polyvinyl pyrrolidone and polyvinyl alcohol of which the degree of polymerization is 700 to 3000.

Effect of the Invention

The present invention can provide a jig for vitrification cryopreservation which has an excellent absorption capability of absorbing extra vitrification solution on dropping the vitrification solution together with a cell or tissue, and is capable of holding reliably the cell or tissue even at the time of freezing or at the time of thawing. The present invention can also provide a jig for vitrification cryopreservation which is excellent in visibility for cell or tissue. Therefore, the present invention makes possible an easy and reliable operation of cryopreservation for cell or tissue.

BRIEF DESCRIPTION OF THE DRAWINGS

In FIG. 6, the holes structure portion of the metallic support is shown by a broken line.

MODE FOR CARRYING OUT THE INVENTION

Figure 1:
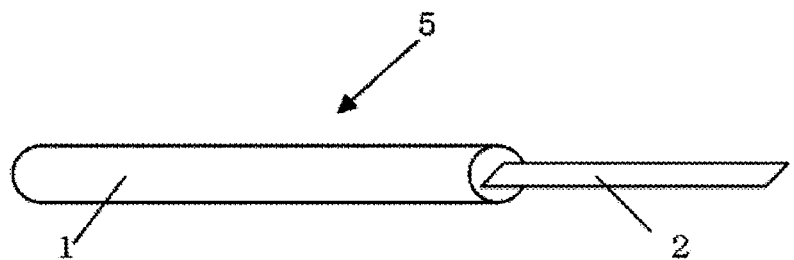
FIG. 1 is an overall view showing an example of the jig for vitrification cryopreservation of cell or tissue.

The jig for vitrification cryopreservation of the present invention is used when a biological cell or tissue is cryopreserved. A cell, herein, includes not only a single cell, but also a cell population composed of a plurality of cells. The cell population composed of a plurality of cells may include a cell population composed of single type of a plurality of cells and a cell population composed of different types of a plurality of cells. A tissue may include a tissue composed of single type of cells, a tissue composed of different types of cells and a tissue containing a non-cellular material such as an extracellular matrix in addition to cells. The jig for vitrification cryopreservation of the present invention is, preferably, intended for allowing the cell or tissue to adhere to the vitrification solution absorber together with a vitrification solution, and for immersing the jig to which the cell or tissue is attached in a cooling solvent such as liquid nitrogen to freeze. Since the vitrification solution absorber mentioned above can give an easy retention of the cell or tissue along with vitrification solution and then can hold reliably the cell or tissue even at the time of freezing or at the time of thawing, it is possible to carry out the immersion operation of the cell or tissue into liquid nitrogen easily. Therefore, the use of the jig for vitrification cryopreservation of the present invention can bring an easy and reliable operation of cryopreservation for cell or tissue. The jig for vitrification cryopreservation of the present invention can be rephrased as a tool for cryopreservation of cell or tissue, a tool for vitrification preservation of cell or tissue, an instrument for cryopreservation of cell or tissue, or an instrument for vitrification preservation of cell or tissue.

The jig for vitrification cryopreservation of the present invention can give a stable survivability of cell or tissue even in the case that an amount to attach with dropwise vitrification solution together with the cell or tissue is large, because the vitrification solution absorber can absorb an extra vitrification solution. Moreover, since the jig is excellent in visibility for the cell or tissue on the vitrification solution absorber, it is possible to easily check the cell or tissue cryopreserved. Furthermore, the jig for vitrification cryopreservation of the present invention can hold reliably the cell and tissue even at the time of freezing or at the time of thawing. Then, by the operation like that, the cell or tissue kept in the vitrification solution absorber is covered in a very small amount of the vitrification solution, which comes to the frozen state quickly on the freezing operation. Furthermore, since the vitrification solution adhering around the cell or tissue is in very small quantities, the vitrification solution can be diluted immediately after thawing the cryopreserved cell or tissue.

In the following, we will explain the constitution of the jig for vitrification cryopreservation of the present invention.

The jig for vitrification cryopreservation of the present invention has a metallic support, and a vitrification solution absorber including an adhesion layer and a vitrification solution-absorbing layer on the metallic support in the order from the side closer to the metallic support. The jig for vitrification cryopreservation of the present invention may be made of the vitrification solution absorber, or may comprise a grip portion described later etc. in conjunction with the vitrification solution absorber unless the effects of the present invention are impaired.

Figure 5:
FIG. 5 is a schematic view showing an example of the vitrification solution absorber arranged on both sides of the metallic support.

The vitrification solution absorber will do as long as it has a metallic support, an adhesion layer and a vitrification solution-absorbing layer in this order, and it may have an adhesion layer and a vitrification solution-absorbing layer in this order on one side of the metallic support, or may also have an adhesion layer and a vitrification solution-absorbing layer on both sides of the metallic support, as exemplified in FIG. 5, for example. The vitrification solution absorber having an adhesion layer and a vitrification solution-absorbing layer on both sides of a metallic support can include a vitrification solution absorber having a vitrification solution-absorbing layer, an adhesion layer, a metallic support, an adhesion layer and a vitrification solution-absorbing layer in this order.

Further, the vitrification solution absorber may have, in at least a part thereof, a structure with a metallic support, an adhesion layer and a vitrification solution-absorbing layer in this order. For example, the vitrification solution absorber may have an adhesion layer and a vitrification solution-absorbing layer on the entire surface of a metallic support, or may have one or more vitrification solution-absorbing layers on a part of a metallic support (an adhesion layer being located between the vitrification solution-absorbing layer and the metallic support). Also, as exemplified in FIG. 7, for example, the vitrification solution absorber may have a part with an adhesion layer and a vitrification solution-absorbing layer or a vitrification solution-absorbing layer, but without a metallic support (in FIG. 7, Holes structure portion 6).

The jig for vitrification cryopreservation of the present invention can rapidly cool a cell or tissue on a vitrification solution absorber at a fast cooling rate due to having a metallic support. The metallic support of the jig for vitrification cryopreservation of the present invention can, for example, include one made of copper, copper alloy, aluminum, aluminum alloy, gold, gold alloy, silver, silver alloy, iron, or stainless steel. Such a metal can rapidly cool a cell or tissue on the vitrification solution absorber due to having a high thermal conductivity. Among them, for example, the metallic support made of copper, stainless steel, or aluminum is preferable, and the metallic support made of copper is more preferable. The metallic support is shaped ordinarily in thin plate or sheet form with a flat surface. The metallic support is preferably 10 µm to 50 mm, more preferably 100 µm to 10 mm in thickness. Surface of the metallic support may be processed by easy adhesion treatment chemically or electrically, or may be roughened, for the purpose of improving the adhesion property with an adhesion layer. Moreover, for the same purpose, the metallic support may have an undercoat layer. The metallic support may have a plurality of holes (e.g., through hole or non-through hole) or an internal cavity portion, for the purpose of improving the cooling efficiency by penetration of a cooling solvent or improving the handling by weight reduction. In one mode of the present invention, for example, it is preferred to use the metallic support having a through-hole in a vertical direction with respect to the surface where the metallic support meets the adhesion layer (in the case of providing an undercoat layer, undercoat layer). In particular, the metallic support has preferably one or more such holes (through hole) because, for example, good visibility can be obtained when the cell or tissue adhering to a vitrification solution-absorbing layer is observed with a transmission microscope. Further, in the case that the metallic support has such a through hole, the ratio of the through hole to the total area of the metallic support may be set arbitrarily unless the effects of the present invention are impaired.

The metallic support, for its excellent thermal conductivity, is effective not only in the improvement of cooling efficiency but also in keeping the cold environment after vitrification freezing due to high thermal accumulation. For example, in the operation of taking out the cell or tissue to immerse in a melting solution after cryopreservation, it can be expected to increase the viability of the cell or tissue because it is possible to keep it on the jig for vitrification cryopreservation at a low temperature for a certain period of time, even when the jig for vitrification cryopreservation with the cell or tissue is taken out from a cryopreservation container and should be left, for example, due to unforeseen circumstances.

As for the adhesion layer involved in the vitrification solution absorber in the present invention, a layer containing polyvinyl alcohol, hydroxyethyl cellulose, polyvinyl pyrrolidone, a water-soluble adhesive material such as starch paste, an adhesive material such as a vinyl acetate-based adhesive material, an acrylic adhesive material, an epoxy adhesive material, a urethane-based adhesive material, a hot melt adhesive material, an elastomeric adhesive material, an instant adhesive material typified by a cyanoacrylate-based adhesive material, a silicone-based adhesive material, a nitrocellulose-based adhesive material, a nitrile rubber-based adhesive material, a styrene-butadiene-based adhesive material, a urea resin-based adhesive material, a styrene-based resin adhesive material, a phenol resin-based adhesive material, or a light curing adhesive material, can be suitably used. One or more species of them may be used.

Additionally, the adhesion layer can also be actively used as part of a vitrification solution-absorbing layer. From this point of view, the adhesion layer preferably contains polyvinyl alcohol, hydroxyethyl cellulose, polyvinyl pyrrolidone, or a water-soluble adhesive material such as starch paste. Furthermore, from the viewpoint of the toxicities of dissolved components and partly released components to the cell or tissue, the adhesion layer preferably contains at least one of polyvinyl alcohol and polyvinyl pyrrolidone as an adhesive material. Especially, containing at least one of polyvinyl pyrrolidone and polyvinyl alcohol with a polymerization degree of 700 to 3000 in the adhesion layer is preferable on the grounds that not only the more excellent capability of absorbing the vitrification solution is exerted, but also the excellent capability thereof can be obtained even in the case of use after the production of the vitrification solution absorber, after the long-term preservation, or after the preservation under a high temperature environment, for example. Note that the polymerization degree in this range allows a completely saponified, an intermediately saponified or a partially saponified polyvinyl alcohol to be used. The desirable saponification degree of polyvinyl alcohol is 85 mol % or more. Also, the adhesion layer can contain some materials such as various matting agents, a surface active agent, and a pH-adjusting agent, other than the adhesive material, unless the effects of the present invention are impaired. In the present invention, the adhesive material is preferably contained in an amount of 80 mass % or more, more preferably 90 mass % or more, furthermore preferably 95 mass % or more relative to the solid content of the adhesion layer. The content in this range of the adhesive material can give a good adhesion of the metallic support and the vitrification solution-absorbing layer.

The method of forming the adhesion layer is not particularly limited, and the adhesion layer can be formed, for example, by preparing a coating solution (a composition) containing the adhesive material mentioned above, and by applying the coating solution onto a metallic support or onto an undercoat layer provided on the support to dry. In the present invention, if the metallic support has the through hole mentioned above (through hole in the vertical direction with respect to the surface where the metallic support meets the adhesion layer (in the case of providing the undercoat layer, undercoat layer)), it is preferred not to form the adhesion layer in the through hole portion.

The solid content of the adhesion layer is preferably in the range of 0.3 to 50 g/m$^2$, more preferably in the range of 0.5 to 10 g/m$^2$.

In the adhesion layer mentioned above, from the viewpoint of adhesiveness, it is preferred that a part of the adhesion layer gains entry into the vitrification solution-absorbing layer to some extent, but the entry of a large amount of the adhesion layer may impair the absorbing capability of the vitrification solution-absorbing layer. For the mode that a part of the adhesion layer gains entry into the vitrification solution-absorbing layer, it is preferred to apply a coating solution containing the adhesive material mentioned above onto the metallic support or onto the undercoat layer provided on the support, and to overlap the vitrification solution-absorbing layer to dry before the coating layer dries up.

As for the vitrification solution-absorbing layer involved in the vitrification solution absorber in the present invention, a paper or a nonwoven fabric can be suitably used. The main component of the paper or the nonwoven fabric is fiber, and the fiber can quickly absorb the vitrification solution by capillary phenomenon. Fiber is preferable because it can keep a lot of vitrification solution in the space between the fibers.

In the case the vitrification solution-absorbing layer is a paper, pulp fiber constituting the paper can include one made from any of hardwoods and softwoods. The pulp fiber may be unbleached or bleached. A bleached virgin pulp fiber is preferably used. Also, the whiteness of the paper used in the vitrification solution-absorbing layer is preferably 60% or more, more preferably 70% or more. The whiteness in this range is preferable because it allows an easy check of attached cell or tissue. The paper having this whiteness can also be obtained from a non-wood-based pulp fiber such as bleached kenaf other than the virgin pulp. Additionally, although the pulp fiber for recycled paper having a lot of coarse fraction may affect the activity or survivability of a cell or cells constituting a tissue through the coarse fraction, even the pulp fiber for recycled paper can be used if the coarse fraction is sufficiently removed and the whiteness thereof becomes 70% or more, for example. The present invention can also use a mixture of various pulp fibers listed above. Note that the whiteness of the pulp fiber may be measured according to the method described in JIS P8123.

In the case the vitrification solution-absorbing layer in the present invention is a paper, in the vitrification solution-absorbing layer, the percentage of adhesion components such as a binder to the whole paper is preferably 10 mass % or less, more preferably 5 mass % or less, particularly preferably 3 mass % or less. The ordinary paper contains inorganic pigments of about 5 to 20 mass % for improvement of writing easiness, etc., and further includes various papermaking chemicals. The percentage of the inorganic pigments to the whole paper is preferably 5 mass % or less, more preferably 3 mass % or less. Also, among the papermaking chemicals, some fluorescent whitening agents, some dyes, some cationic sizing agents, for example, may affect the activity or survivability of a cell or cells constituting a tissue. Therefore, the percentage of these components to the whole paper is also preferably 1 mass % or less.

In the case the vitrification solution-absorbing layer in the present invention is a nonwoven fabric, in the nonwoven fabric, the percentage of adhesion components such as a binder to the whole nonwoven fabric is preferably 20 mass % or less, more preferably 10 mass % or less, in particular preferably 5 mass % or less.

The nonwoven fabric used in the present invention will be described in detail. In common with the paper mentioned above, there is a fiber used suitably for the nonwoven. The fiber used suitably can include: a cellulosic fiber such as cellulose fiber, rayon fiber and Cuprammonium fiber regenerated from cellulose fiber, and moreover acetate fiber semi-synthesized from cellulose fiber; a synthetic fiber such as polyester fiber, nylon fiber, acrylic fiber, polypropylene fiber, polyethylene fiber, polyvinyl chloride fiber, vinylidene fiber, polyurethane fiber, vinylon fiber, polyvinyl fiber, fluorocarbon resin fiber; an inorganic fiber such as glass fiber, ceramic fiber, titanium potassium fiber; silk fiber and the like. Among them, from the viewpoint of the absorption capability, a cellulosic fiber, a synthetic fiber, glass fiber, etc. are preferable. Cellulose fiber, rayon fiber, Cuprammonium fiber, acetate fiber, vinylon fiber, nylon fiber, polypropylene fiber, polyethylene fiber, glass fiber can be more suitably used.

In the case the vitrification solution-absorbing layer in the present invention is a nonwoven fabric, a nonwoven fabric in which the various suitable fibers mentioned above are mixed can also be used. Furthermore, a nonwoven fabric of a two-layer structure consisting of different fiber components produced by papermaking combining technology of the wet-papermaking method, and a product of a two-layer structure bond-processed with an adhesive agent, can be used.

Then, the preferred method of producing a nonwoven fabric used in the present invention will be described. Regarding the nonwoven fabric, there are various production methods different from paper, and, for example, the following production method is suitably used. The production of the nonwoven fabric includes typically two steps when roughly divided: the step of arranging fibers, and the step of twisting and binding the fibers to each other. The method of arranging the fibers can include a wet method, a dry method, and the like, for example, and other methods can include a spun bond method in which the fiber is produced directly from a resin pellet and at the same time is bound, and a melt-blow method. The wet method includes a thermal bonding method, a chemical bonding method, a hydroentangling method (Spun lace method) and the like in which the fiber is dispersed in water and then the fiber by arranging with a papermaking-up, in the same manner as the papermaking process, is twisted or bound. The dry method produces typically a nonwoven fabric with applications of twisting and binding by thermal bonding method, chemical bonding method, hydroentangling method, or needle punching method after arranging the fibers with a machine called Card. The nonwovens produced by any of these methods can also be used in the present invention.

It is preferred that the nonwoven fabric used for the vitrification solution-absorbing layer is produced without an adhesive agent. More specifically, the nonwoven fabric produced by spun bond method or melt-blow method, and further the nonwoven fabric produced by hydroentangling method or needle punching method after the fibers are arranged in a wet method or a dry method, among the production methods mentioned above, can be suitably used. These production methods can bind the fibers to each other without an adhesion component such as a binder, and can produce the nonwoven fabric made of 100% fiber, for example. Like that, the nonwoven fabric consisting of fibers can be suitably used for the vitrification solution-absorbing layer in the present invention. In the case of the production using cellulose fiber, rayon fiber, Cuprammonium fiber, acetate fiber, nylon fiber, polypropylene fiber, polyethylene fiber, etc., which fibers are especially most suitable ones used in the present invention, a hydroentangling method or a needle punching method is most suitable for the production method, regardless of a wet method or a dry method.

The vitrification solution-absorbing layer of the present invention, from the viewpoint of the ability to absorb vitrification solution, is preferably 10 μm or more, more preferably 50 μm or more in thickness. The upper limit of the thickness is 1 cm or less. Also, the vitrification solution-absorbing layer is preferably 10 $g/m^2$ or more, more preferably 20 $g/m^2$ or more in basis weight. The upper limit of the basis weight is preferably 1 $kg/m^2$ or less. Adjusting the thickness in such a range to the cell or tissue cryopreserved can offer an easy adjustment of absorption capacity of the vitrification solution-absorbing layer depending on the amount of vitrification solution to be dropped.

The vitrification solution-absorbing layer of the present invention, from the viewpoint of the absorption capability and the cooling rate for the vitrification solution, is preferably 0.5 $g/cm^3$ or less, more preferably 0.25 $g/cm^3$ or less in density. In such a range of the density, the space volume within the vitrification solution-absorbing layer is large, and a high absorption capability of the vitrification solution-absorbing layer is exerted. The lower limit of the density of the vitrification solution-absorbing layer is preferably 0.05 g/cm$^3$ or more, in general.

In the vitrification solution absorber in the present invention, in the case the vitrification solution-absorbing layer is a paper or a nonwoven fabric, the absorber can carry a holes structure portion without a metallic support in the under portion of the vitrification solution-absorbing layer in a vertical direction with respect to the surface where the metallic support meets the adhesion layer (in the case of providing an undercoat layer, undercoat layer), in the part where the cell or tissue adheres to the vitrification solution-absorbing layer, in order to observe the cell or tissue on the jig for vitrification cryopreservation using a transmission microscope. Such a vitrification solution absorber can be produced, for example, by using a metallic support with a through hole in a vertical direction with respect to the surface where the metallic support meets the adhesion layer (in the case of providing an undercoat layer, undercoat layer). Since the vitrification solution-absorbing layer in the range of, for example, 0.5 g/cm$^3$ or less in density and 100 g/m$^2$ or less in basis weight obtains a total light transmittance to some extent at the attachment time of the vitrification solution, it allows transmission of light emitted from a microscope light source at the holes structure portion and improves visibility of the cell or tissue on the jig for vitrification cryopreservation. Then, the cell or tissue can be easily checked. For the holes structure portion, it is preferred that the vitrification solution-absorbing layer in the upper portion of the holes structure portion does not have an adhesion layer in the under portion thereof.

The vitrification solution absorber of which the vitrification solution-absorbing layer is 0.5 g/cm$^3$ or less in density and 100 g/m$^2$ or less in basis weight and which has a holes structure portion without a metallic support in the under portion of the vitrification solution-absorbing layer, is one of preferable embodiments in the present invention. The jig for vitrification cryopreservation having such a vitrification solution absorber is suitably used, for example, in the case of checking the cell or tissue on the jig for vitrification cryopreservation with a transmission microscope. The vitrification solution-absorbing layer is preferably 0.05 to 0.5 g/cm$^3$ in density and 10 to 100 g/m$^2$ in basis weight. The vitrification solution-absorbing layer in these ranges of density and basis weight further improves visibility of the cell or tissue on the jig for vitrification cryopreservation in the observation with a transmission microscope.

The shape and size of the holes structure portion mentioned above are not particularly limited, and may be set appropriately according to the size etc. of the cell or tissue subjected to cryopreservation.

Further, in another preferred embodiment, it is preferred that the vitrification solution-absorbing layer contains a fiber of 4 µm or less in average fiber diameter. That is because the vitrification solution-absorbing layer containing a fiber of 4 µm or less in average fiber diameter improves the visibility of the cell or tissue when using a reflection type microscope. More preferably, the vitrification solution-absorbing layer contains a fiber of 0.01 to 4 µm in average fiber diameter, furthermore preferably, 0.02 to 4 µm in average fiber diameter. The vitrification solution-absorbing layer containing such a fiber further improves visibility of the cell or tissue on the jig for vitrification cryopreservation in the observation with a reflection type microscope.

Note that the average fiber diameter in the present invention means an average of values obtained by taking a photo of the vitrification solution absorber using a scanning electron microscope and by measuring the diameters of thirty fibers arbitrarily selected from the photo image.

As the vitrification solution-absorbing layer containing a fiber of 4 µm or less in average fiber diameter, for example, a paper or a nonwoven fabric containing such a fiber is suitably used. For example, a nonwoven fabric or a paper in which such fibers are randomly arranged is preferable. The percentage of the fiber of 4 µm or less in average fiber diameter contained in the vitrification solution-absorbing layer is preferably 80 mass % or more, more preferably 90 mass % or more, furthermore preferably 95 mass % or more, relative to the vitrification solution-absorbing layer. Also, for the vitrification solution-absorbing layer, it is preferred that the fibers constituting the layer should be one by one independently dispersed without forming a bundle. A method of processing fibers of 4 µm or less in average fiber diameter into a nonwoven fabric form so as not to form a bundle can include, for example, a melt-blown method, a hydroentangling method, and an electro-spinning method.

A method of processing fibers of 4 µm or less in average fiber diameter into a paper form so as not to form a bundle can include, for example, in the case of using cellulose fiber, a method as described in JP-A-2006-193858 etc., which produces the paper using a dispersion solution prepared by dispersing the fibers of which the hydrogen bonding force between the cellulose fibers is weakened with the addition of alcohols of various types to the cellulose fiber. Such a method can provide the vitrification solution-absorbing layer with a high ability to absorb vitrification solution, by using a fiber of 4 µm or less in average fiber diameter. Further, since an inorganic fine fiber such as glass fiber does not have a strong hydrogen bond or the like ordinarily, it can provide the vitrification solution absorber with a high ability to absorb vitrification solution even by using an ordinary papermaking method.

The area of the vitrification solution-absorbing layer in the present invention is not particularly limited, and may be set appropriately according to dropping amount of the vitrification solution to be dropped together with the cell or tissue, etc., but it is preferably set to 40 to 40000 mm$^2$, for example.

The vitrification solution-absorbing layer in the present invention may be formed on the entire surface of the vitrification solution absorber or may be formed on a part thereof. Also, in the case the vitrification solution absorber has a number of portions of the vitrification solution-absorbing layer as mentioned later, it is preferred that one of the successive vitrification solution-absorbing layer portions has said area.

Hereinbefore, the vitrification solution absorber in the present invention has been described. The constitution of the jig for vitrification cryopreservation of the present invention will be described below. The jig for vitrification cryopreservation of the present invention will do as long as it has the vitrification solution absorber mentioned above, but it may connect the vitrification solution absorber to a grip portion. Having the grip portion is preferable for providing a good workability at the time of freezing.

FIG. 1 is an overall view showing an example of the jig for vitrification cryopreservation of cell or tissue, pertinent to the present invention. Jig for vitrification cryopreservation 5 in FIG. 1 comprises Grip portion 1 and Vitrification solution absorber 2. Grip portion 1 is preferably made of a material resistible to liquid nitrogen. As such a material, for example, various metals such as aluminum, iron, copper, stainless steel alloys; plastics such as ABS resin, polypropylene resin, polyelene resin, fluorine resins, various engineering plastics; or glass can be suitably used. Also, basically, Vitrification solution absorber 2 is preferably formed in strip or sheet for the handling.

The method of connecting Grip portion 1 and Vitrification solution absorber 2 in FIG. 1 will be explained. The connection method is not particularly limited, but, for example, if Grip portion 1 is a resin, Vitrification solution absorber 2 can be connected to Grip portion 1 by insert molding at the time of the forming process. Furthermore, if a vitrification solution absorber insertion site not shown in Figure is prepared in Grip portion 1, Vitrification solution absorber 2 can be connected to Grip portion 1 with an adhesive agent. As for the adhesive agent, various ones can be used, and a silicone-based adhesive agent strong in low temperature, a fluorine-based adhesive agent or the like can be suitably used.

When a cell or tissue is cryopreserved for a long period with the jig for vitrification cryopreservation of cell or tissue, pertinent to the present invention, it is also possible to cap the jig shown in FIG. 1 or to enclose the jig in a container to seal for shielding the cell or tissue from the outside, for safety. Moreover, when a cell or tissue is cryopreserved in direct contact with liquid nitrogen, even if the jig for vitrification cryopreservation is sterilized, the sterile condition of the jig may not be guaranteed, because a liquid nitrogen is not usually sterilized. With that, there are cases where the vitrification solution absorber with the cell or tissue attached before freezing is capped or the jig for vitrification cryopreservation in a container is enclosed to seal and a cell or tissue is cryopreserved not in direct contact with liquid nitrogen. In addition, the freezing method without direct contact with liquid nitrogen as mentioned above predominates in overseas developed countries such as Europe. For such a reason, it is preferred that the cap and the container are prepared with various metals, various resins, glass, ceramic, etc. which are materials resistible to liquid nitrogen. The shape is not particularly limited, and the cap may be one of any shapes as long as it does not come in contact with the vitrification solution absorber and can shield the cell or tissue from the outside, such as a half-spindle-shaped cap like a pencil cap, a dome-like cap, a cylindrical straw cap, etc., for example. The shape of the container is not particularly limited, and the container will do as long as it does not come in contact with the cell or tissue on the vitrification solution absorber and can cover or store the jig for vitrification cryopreservation to seal.

In the present invention, the jig for vitrification cryopreservation can be used in combination with the cap or the container which can shield the cell or tissue on the vitrification solution absorber from the outside, unless the effects of the present invention are impaired.

Figure 2:
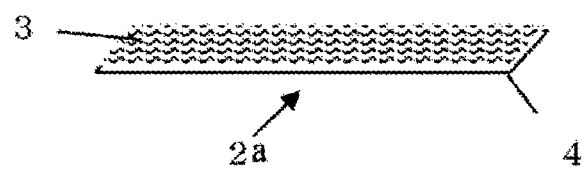
FIG. 2 is an enlarged view of the vitrification solution absorber in FIG. 1.

An example of the vitrification solution absorber in the present invention is illustrated in FIG. 2. FIG. 2 is an enlarged view of the vitrification solution absorber in FIG. 1. Vitrification solution absorber 2a of FIG. 2 has Vitrification solution-absorbing layer 3 on Metallic support 4. In the meantime, the adhesion layer is not shown. Vitrification solution absorber 2a shown in FIG. 2 is an example of mode having Vitrification solution-absorbing layer 3 on the entire surface of the vitrification solution absorber.

Figure 3:
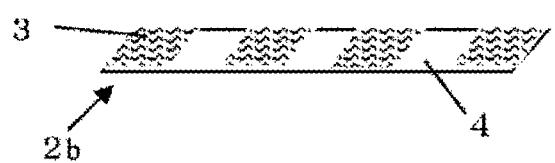
FIG. 3 is a schematic view showing an example of the vitrification solution absorber used in the case that a number of cells or tissues are cryopreserved with one of the jigs for vitrification cryopreservation.
Figure 4:
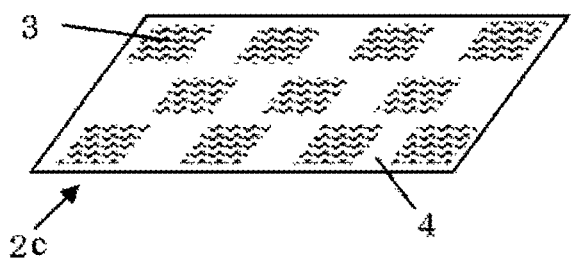
FIG. 4 is a schematic view showing another example of the vitrification solution absorber used in the case that a number of cells or tissues are cryopreserved with one of the jigs for vitrification cryopreservation.

FIGS. 3 to 6 show examples of other embodiments of the vitrification solution absorber in the present invention. The vitrification solution absorber of the jig for vitrification cryopreservation of cell or tissue shown in FIG. 1 can be replaced with one shown in FIGS. 3 to 6. In the meantime, FIGS. 3 to 6 do not show the adhesion layer, either, in the same manner as FIG. 2. FIG. 3 is a schematic view showing an example of the vitrification solution absorber which can be suitably used in the case of cryopreserving a number of cells or a tissue with one of the jigs for vitrification cryopreservation. And FIG. 4 is a schematic view showing another example of the vitrification solution absorber which can be suitably used in the case of cryopreserving a number of cells or a tissue with one of the jigs for vitrification cryopreservation. In FIG. 3 and FIG. 4, a number of Vitrification solution-absorbing layers 3 are discontinuous and arranged on the metallic support 4.

In the case of Vitrification solution-absorbing layer 3 as shown in FIG. 2 mentioned above being a continuous shape, there is a case where the absorbency for vitrification solution is decreased, for example, when a second cell or a tissue is made to adhere to Vitrification solution-absorbing layer 3, because the vitrification solution usually spreads in the lateral direction and the thickness direction in the vitrification solution-absorbing layer when trying to attach a number of cells or a tissue to Vitrification solution-absorbing layer 3. However, as shown in FIG. 3 and FIG. 4, a number of Vitrification solution-absorbing layers 3 discontinuously arranged on Metallic support 4 allow the cell or tissue together with vitrification solution to firmly adhere one by one to Vitrification solution-absorbing layers 3 without the above problem. In FIG. 3 and FIG. 4, as an example, a number of Vitrification solution-absorbing layers 3 shaped in square are arranged. Vitrification solution absorber 2b and Vitrification solution absorber 2c shown in FIG. 3 and FIG. 4 are also examples of the vitrification solution absorber having the vitrification solution-absorbing layer on a part of the metallic support.

FIG. 5 is a schematic view of the vitrification solution absorber of which the vitrification solution-absorbing layer is arranged on both sides of the metallic support, for workability and improvement of promptness during freezing or thawing of the cell or tissue. The arrangement of Vitrification solution-absorbing layer 3 on both sides of Metallic support 4 can provide a quick drop and attachment of the cell or tissue in a moment without worrying about the front or back.

Figure 6:
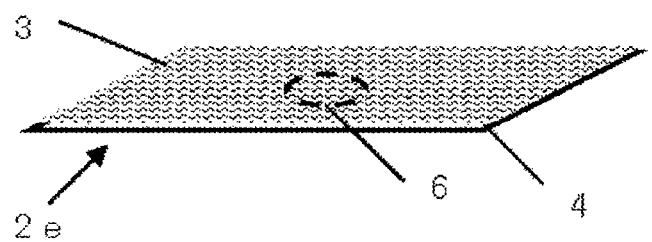
FIG. 6 is a schematic view showing an example of the vitrification solution absorber in which a holes structure portion (through hole) is set in apart of the metallic support.
Figure 7:
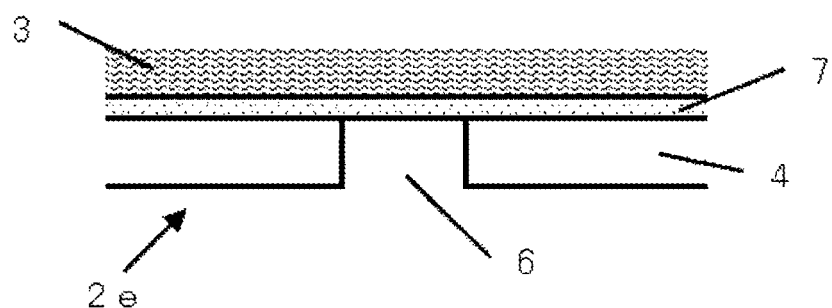
FIG. 7 is a schematic view showing a cut surface structure in a vertical direction with respect to the surface where the adhesion layer meets the vitrification solution-absorbing layer, in the region including the holes structure portion of the vitrification solution absorber illustrated in FIG. 6.
Figure 8:
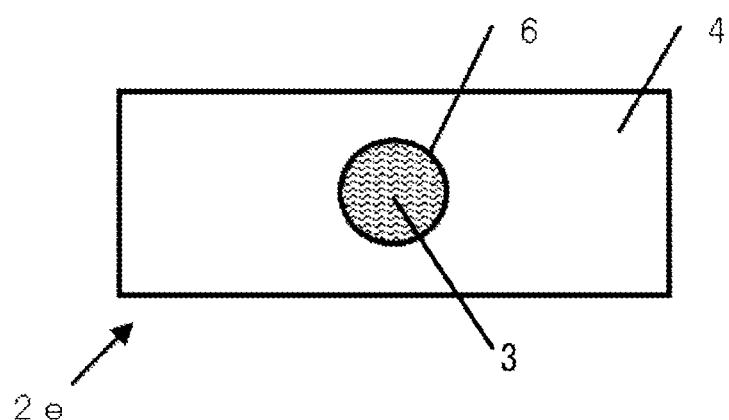
FIG. 8 is a schematic view when the vitrification solution absorber illustrated in FIG. 6 is viewed from the opposite side of the metallic support side.

FIG. 6 is a schematic view of Vitrification solution absorber 2e in which Holes structure portion 6 is arranged on a part of Metallic support 4, in order to give a visual observability of cell or tissue under a transmission microscope. FIG. 6 shows a schematic view of Vitrification solution absorber 2e when viewed from the side of Vitrification solution-absorbing layer 3. The arrangement of Holes structure portion 6 (portion indicated by broken line in FIG. 6) allows the cell or tissue on Vitrification solution-absorbing layer 3 placed in the upper part of the holes structure portion (through hole provided in the metallic support) to be observed with a transmission microscope. FIG. 7 is a schematic view of a cutting surface structure (cross-sectional structure in a vertical direction with respect to the surface where the metallic support meets the adhesion layer). FIG. 8 is a schematic view of Vitrification solution absorber 2e shown in FIG. 6 when viewed from Metallic support 4 side opposite to the vitrification solution-absorbing layer.

The jig for vitrification cryopreservation of the present invention is suitably used in cryopreserving a cell or tissue by vitrification preservation method. For example, it is suitably used in cryopreserving a cell or tissue in the same manner as Cryo top method used in the case of cryopreserving an ovum or embryo. With the jig for vitrification cryopreservation of the present invention, the cell is hardly damaged by the vitrification solution outside the cell during freezing and during thawing of the cell or tissue, and the cell or tissue can be cryopreserved with an excellent survival rate.

The method of cryopreserving a cell or tissue using the jig for vitrification cryopreservation of the present invention is not particularly limited, and first, drops the cell or tissue immersed in a vitrification solution together with the vitrification solution onto the vitrification solution-absorbing layer placed on the vitrification solution absorber, and absorbs the vitrification solution adhering around the cell or tissue, for example. Then, after the vitrification solution absorber is immersed in liquid nitrogen or the like while holding the cell or tissue on the vitrification solution absorber, the cell can be frozen. In this step, after a cap which can shield the cell or tissue on the vitrification solution absorber mentioned above from the outside is set to the vitrification solution absorber or after the jig for vitrification cryopreservation is enclosed in a container as mentioned above to seal, it is also possible to immerse the vitrification solution absorber in liquid nitrogen or the like. For the vitrification solution, one used for ordinary freezing of cell is usable, and an aqueous solution containing one or more of various cryoprotective agents such as glycerol, ethylene glycol, and DMSO (dimethylsulfoxide) can be used. For conditions, etc. on immersing a cell or tissue into a vitrification solution, and on immersing a cell or tissue into liquid nitrogen, ones employed usually in vitrification freezing methods are employable.

The amount of vitrification solution dropped together with a cell or tissue in cryopreserving it using the jig for vitrification cryopreservation of the present invention, is not particularly limited, and the amount can be appropriately selected depending on type of cells or tissues, materials, thickness, density, etc. of the vitrification solution-absorbing layer. In consideration of the area of the vitrification solution absorber mentioned above, operability of micropipette, etc., for example, an amount of 0.3 to 5 µL is preferable, more preferably 0.5 to 3 µL.

A cell that can be cryopreserved with the jig for vitrification cryopreservation of the present invention can include, for example, a reproductive cell such as ovum and embryo, a sperm of mammals (e.g., humans (human), cow, pig, horse, rabbit, rat, mouse, etc.); a pluripotent stem cell such as an Induced pluripotent stem cell (iPS cell), and Embryonic stem cell (ES cell). In addition, a cultured cell such as a primary cultured cell, a subcultured cell, and a cell line cell can be included. Moreover, the cell, in one or more embodiments, can include a fibroblast, a cancer-originated cell such as pancreatic cancer, liver cancer; an adherent cell such as epithelial cell, vascular endothelial cell, lymphatic endothelial cell, nerve cell, cartilage cell, tissue stem cell, and immune cell. Furthermore, a tissue which can be cryopreserved can include a tissue composed of a homologous or heterologous cell, such as ovary, skin, corneal epithelium, periodontal, and cardiac muscle. The present invention, in particular, is suitable for vitrification cryopreservation of a tissue with a sheet-like structure (e.g., a cell sheet, a skin tissue). The jig for vitrification cryopreservation of the present invention can also be suitably used for vitrification cryopreservation of not only a tissue taken directly from a living body, but also, for example, a cultured skin proliferated by culturing in vitro, what is called a cell sheet constructed in vitro, and an artificial tissue like a tissue model having a three-dimensional structure which is described in Kokai JP-A-2012-205516. The jig for vitrification cryopreservation of the present invention is suitably used as the jig for vitrification cryopreservation of cell or tissue as mentioned above.

EXAMPLES

The following further illustrates in more detail the present invention with examples and the present invention is demonstrated, but the present invention is not limited to the following examples.

Example 1

<Preparation of Vitrification Solution Absorber>

A 5 mass % aqueous solution of PVA617, trade name, manufactured by Kuraray Co., Ltd. (a saponification degree of 95-96 mol %, a polymerization degree of polyvinyl alcohol of 1700), as an adhesion layer, was applied with 4 g/m$^2$ in mass at the time of drying, on a copper support having 300 µm in thickness. Before drying of the coating layer, Bemliese (registered trademark) SA14G (70 µm in thickness, 14 g/m$^2$ in basis weight, 0.20 g/cm in density), a nonwoven fabric composed of cellulose (Cupra) fiber, manufactured by Asahi Kasei Fibers Co., Ltd., as a vitrification solution-absorbing layer, was lapped over the coating layer to be dried. As mentioned above, the vitrification solution absorber of Example 1 having the adhesion layer and the vitrification solution-absorbing layer in this order on the metallic support was prepared.

Example 2

<Preparation of Vitrification Solution Absorber>

The vitrification solution absorber of Example 2 was prepared, in the same manner as in Example 1, except for using Bemliese (registered trademark) SA28G (130 µm in thickness, 28 g/m$^2$ in basis weight, 0.22 g/cm$^3$ in density), a nonwoven fabric composed of cellulose (Cupra) fiber, manufactured by Asahi Kasei Fibers Co., Ltd., as a vitrification solution-absorbing layer.

Example 3

<Preparation of Vitrification Solution Absorber>

The vitrification solution absorber of Example 3 was prepared, in the same manner as in Example 1, except for using Bemliese (registered trademark) SA30G (250 µm in thickness, 30 g/m$^2$ in basis weight, 0.12 g/cm$^3$ in density), a nonwoven fabric composed of cellulose (Cupra) fiber, manufactured by Asahi Kasei Fibers Co., Ltd., as a vitrification solution-absorbing layer.

Example 4

<Preparation of Vitrification Solution Absorber>

The vitrification solution absorber of Example 4 was prepared, in the same manner as in Example 1, except for using Bemliese (registered trademark) SA50U (500 µm in thickness, 50 g/m$^2$ in basis weight, 0.10 g/cm$^3$ in density), a nonwoven fabric composed of cellulose (Cupra) fiber, manufactured by Asahi Kasei Fibers Co., Ltd., as a vitrification solution-absorbing layer.

Example 5

<Preparation of Vitrification Solution Absorber>

The vitrification solution absorber of Example 5 was prepared, in the same manner as in Example 1, except for using Bemliese (registered trademark) SE103 (540 μm in thickness, 100 g/m² in basis weight, 0.19 g/cm³ in density), a nonwoven fabric composed of cellulose (Cupra) fiber, manufactured by Asahi Kasei Fibers Co., Ltd., as a vitrification solution-absorbing layer.

Example 6

<Preparation of Vitrification Solution Absorber>

The vitrification solution absorber of Example 6 was prepared, in the same manner as in Example 1, except for using Elleair (registered trademark) Prowipe Soft Micro Wiper 5220 (160 μm in thickness, 22 g/m² in basis weight, 0.14 g/cm³ in density), a paper, manufactured by Daio Paper Corporation, as a vitrification solution-absorbing layer.

Example 7

<Preparation of Vitrification Solution Absorber>

The vitrification solution absorber of Example 7 was prepared, in the same manner as in Example 1, except for using BFNNO.1, trade name (50 μm in thickness, 12 g/m² in basis weight, 0.24 g/cm³ in density), a nonwoven fabric composed of vinylon fiber, manufactured by Kuraray Co., Ltd., as a vitrification solution-absorbing layer.

Example 8

<Preparation of Vitrification Solution Absorber>

The vitrification solution absorber of Example 8 was prepared, in the same manner as in Example 1, except for using D-17 (70 μm in thickness, 17 g/m² in basis weight, 0.24 g/cm³ in density), a nonwoven fabric composed of cellulose (rayon) fiber, manufactured by Miki Tokushu Paper Mfg. Co., Ltd., as a vitrification solution-absorbing layer.

Example 9

<Preparation of Vitrification Solution Absorber>

The vitrification solution absorber of Example 9 was prepared, in the same manner as in Example 1, except for using S-17 (70 μm in thickness, 17 g/m² in basis weight, 0.24 g/cm³ in density), a nonwoven fabric composed of a fiber mixture of PET fiber and cellulose (rayon) fiber, manufactured by Miki Tokushu Paper Mfg. Co., Ltd., as a vitrification solution-absorbing layer.

Example 10

<Preparation of Vitrification Solution Absorber>

The vitrification solution absorber of Example 10 was prepared, in the same manner as in Example 3, except for using a stainless steel support having 300 μm in thickness, instead of the copper support with 300 μm in thickness.

Example 11

<Preparation of Vitrification Solution Absorber>

The vitrification solution absorber of Example 11 was prepared, in the same manner as in Example 3, except for using an aluminum support having 300 μm in thickness, instead of the copper support with 300 μm in thickness.

Comparative Example 1

<Preparation of Vitrification Solution Absorber>

A transparent PET film (250 μm in thickness), a colorless transparent film, was directly used as the vitrification solution absorber of Comparative Example 1.

Comparative Example 2

<Preparation of Vitrification Solution Absorber>

No. 5C (210 μm in thickness, 12 g/m² in basis weight, 0.57 g/cm³ in density), a filter paper, manufactured by Advantec, was directly used as the vitrification solution absorber of Comparative Example 2.

Comparative Example 3

<Preparation of Vitrification Solution Absorber>

No. 2 (450 μm in thickness, 124 g/m² in basis weight, 0.28 g/cm³ in density), a filter paper, manufactured by Advantec, was directly used as the vitrification solution absorber of Comparative Example 3.

Comparative Example 4

<Preparation of Vitrification Solution Absorber>

No. 7 (170 μm in thickness, 90 g/m² in basis weight, 0.53 g/cm³ in density), a filter paper, manufactured by Advantec, was directly used as the vitrification solution absorber of Comparative Example 4.

Comparative Example 5

<Preparation of Vitrification Solution Absorber>

Bemliese (registered trademark) SA28G (130 μm in thickness, 28 g/m² in basis weight, 0.22 g/cm³ in density), a nonwoven fabric composed of cellulose (Cupra) fiber, manufactured by Asahi Kasei Fibers Co., Ltd., was directly used as the vitrification solution absorber of Comparative Example 5.

Comparative Example 6

<Preparation of Vitrification Solution Absorber>

Bemliese (registered trademark) SA28G (130 μm in thickness, 28 g/m² in basis weight, 0.22 g/cm³ in density), a nonwoven fabric composed of cellulose (Cupra) fiber, manufactured by Asahi Kasei Fibers Co., Ltd., was placed on a copper support with 300 μm in thickness, which was used as the vitrification solution-absorbing layer of Comparative Example 6, wherein the vitrification solution-absorbing layer and the support were not bonded.

Comparative Example 7

<Preparation of Vitrification Solution Absorber>

A copper metallic plate with 300 μm in thickness was directly used as the vitrification solution absorber of Comparative Example 7.

<Evaluation of Absorbability for Vitrification Solution 1>

Each of the vitrification solution absorbers of Examples 1 to 11 and Comparative Examples 1 to 7 was cut into a strip form of 5 mm in width and 50 mm in length. Each of the cut vitrification solution absorbers was placed with the vitrification solution-absorbing layer facing upward. As a vitrification solution, a composition containing a 20 volume % serum, a 15 volume % DMSO, a 15 volume % ethylene glycol, and a 0.2 volume % sucrose in the modified TCM199 medium manufactured by Sigma-Aldrich, was used. To check the absorption rate of the vitrification solution absorber, 2 µL of the vitrification solution of the composition mentioned above was made to adhere dropwise with a micropipette onto the vitrification solution-absorbing layer of the vitrification solution absorber which had been cut into the strip form. After the attachment dropwise, the state of droplets of the vitrification solution attached onto the vitrification solution absorber was visually observed and the absorbability was evaluated by the following criteria.

Evaluation of absorbability for vitrification solution 1 was made according to the following criteria.

⊙: After the attachment of the vitrification solution dropwise, the vitrification solution was all absorbed within less than 10 seconds.
○: After the attachment of the vitrification solution dropwise, the vitrification solution was almost all absorbed within less than 10 seconds.
x: After the attachment of the vitrification solution dropwise, it took 10 seconds or more to absorb the vitrification solution. Or the vitrification solution was not absorbed.
<Evaluation of Absorbability for Vitrification Solution 2>

Each of the vitrification solution absorbers of Examples 1 to 11 and Comparative Examples 1 to 7 was cut into a 50 mm square. Each of the cut vitrification solution absorbers was placed with the vitrification solution-absorbing layer facing upward. As a vitrification solution, a composition containing a 20 volume % serum, a 15 volume % DMSO, a 15 volume % ethylene glycol, and a 0.2 volume % sucrose in the modified TCM199 medium manufactured by Sigma-Aldrich, was used. To check the absorption rate of the vitrification solution absorber, 500 µL of vitrification solution of the composition mentioned above was made to adhere dropwise with a micropipette onto the vitrification solution-absorbing layer of the vitrification solution absorber which had been cut into the 50 mm square. After 10 seconds from the attachment dropwise, the vitrification solution absorber was picked up with tweezers and flipped front and back (top and bottom), and whether the vitrification solution kept in the vitrification solution absorber dripped was evaluated by the following criteria.

Evaluation of absorbability for vitrification solution 2 was evaluated according to the following criteria.

⊙): The dripping, etc. is not observed at all and the vitrification solution uniformly penetrated into the entirety of the vitrification solution-absorbing layer.
○: The dripping, etc. is slightly observed and the vitrification solution almost uniformly penetrated into the entirety of the vitrification solution-absorbing layer.
x: The dripping is clearly observed when the front and back are flipped.
<Immersion Evaluation in Cooling Solvent>

Each of the vitrification solution absorbers of Examples 1 to 11 and Comparative Examples 1 to 7 was cut into a strip form of 5 mm in width and 50 mm in length. Each of the cut vitrification solution absorbers was placed with the vitrification solution-absorbing layer facing upward. As a vitrification solution, a composition containing a 20 volume % serum, a 15 volume % DMSO, a 15 volume % ethylene glycol, and a 0.2 volume % sucrose in the modified TCM199 medium manufactured by Sigma-Aldrich, was used. Two µL of vitrification solution of the composition mentioned above was made to adhere dropwise with a micropipette onto the vitrification solution-absorbing layer of the vitrification solution absorber which had been cut into the strip form. After 10 seconds from the dropping of the vitrification solution, one end of the vitrification solution absorber was grasped with tweezers, and the vitrification solution absorber was immersed for 30 seconds in liquid nitrogen. After the immersion, the vitrification solution absorber was taken out to be put in room temperature environment. Then, whether there was a deformation or damage of the vitrifaction solution absorber in comparison with one before the immersion in liquid nitrogen was visually observed, and the durability in the actual use was evaluated by the following criteria.

Immersion Evaluation in cooling solvent was evaluated according to the following criteria.
○: The deformation or damage of the vitrification solution absorber cannot be observed at all.
x: The deformation or damage of the vitrification solution absorber is observed, and it cannot withstand practical use.
<Evaluation of Visibility 1>

To check the visibility of the cell on the vitrification solution-absorbing layer with a transmission microscope, in the vitrification solution absorbers of Examples 1 to 11 and Comparative Example 6 having a metallic support, the vitrification solution absorber of an embodiment shown in FIG. 6, in which a holes structure portion (2 mm circle in diameter) was arranged in a part of the metallic support, was prepared. Each of the prepared vitrification solution absorbers was placed with the vitrification solution-absorbing layer facing upward. In the evaluation, glass beads of 0.1 mm in diameter as pseudo-cells were made to drop to adhere together with a vitrification solution onto the vitrification solution-absorbing layer located in the upper part of the holes structure portion, and whether or not the glass beads on the vitrification solution-absorbing layer could be visible with a transmission microscope (manufactured by Olympus Corporation, SZH-121) was evaluated according to the following criteria. As the vitrification solution, a composition containing a 20 volume % serum, a 15 volume % DMSO, a 15 volume % ethylene glycol, and a 0.2 volume % sucrose in the modified TCM199 medium manufactured by Sigma-Aldrich, was used. Incidentally, for Comparative Examples 2 to 5 without a support, the glass beads attached dropwise onto the vitrification solution-absorbing layer were observed with the transmission microscope and evaluated, and for Comparative Example 1 or 7 without an absorbing layer, the glass beads attached dropwise onto the support were observed with the transmission microscope and evaluated.

Visibility evaluation was made according to the following criteria.
○: The form of pseudo-cells can be easily checked.
x: It is difficult or impossible to check the presence of pseudo-cells.

The results of Evaluations of absorbability for vitrification solution 1 and 2, Immersion evaluation in cooling solvent, and Evaluation of visibility mentioned above will be shown in Table 1.

TABLE 1

|  | Evaluation of absorbability for vitrification solution 1 | Evaluation of absorbability for vitrification solution 2 | Immersion evaluation in cooling solvent | Evaluation of visibility |
|---|---|---|---|---|
| Example 1 | ○ | ○ | ○ | ○ |
| Example 2 | ⊙ | ⊙ | ○ | ○ |
| Example 3 | ⊙ | ⊙ | ○ | ○ |
| Example 4 | ⊙ | ⊙ | ○ | ○ |
| Example 5 | ⊙ | ⊙ | ○ | ○ |
| Example 6 | ⊙ | ⊙ | ○ | ○ |
| Example 7 | ○ | ○ | ○ | ○ |
| Example 8 | ○ | ○ | ○ | ○ |
| Example 9 | ○ | ○ | ○ | ○ |

TABLE 1-continued

| | Evaluation of absorbability for vitrification solution 1 | Evaluation of absorbability for vitrification solution 2 | Immersion evaluation in cooling solvent | Evaluation of visibility |
|---|---|---|---|---|
| Example 10 | ⊚ | ○ | ○ | ○ |
| Example 11 | ⊚ | ○ | ○ | ○ |
| Comparative example 1 | X | X | ○ | ○ |
| Comparative example 2 | ⊚ | ○ | X | X |
| Comparative example 3 | ⊚ | ○ | X | X |
| Comparative example 4 | ⊚ | ○ | X | X |
| Comparative example 5 | ⊚ | ○ | X | ○ |
| Comparative example 6 | ⊚ | ○ | X | ○ |
| Comparative example 7 | X | X | ○ | X |

The vitrification solution absorbers of Examples 1 to 11 of the present invention had an excellent ability to absorb vitrification solution. Moreover, even when immersed in liquid nitrogen, they were not deformed nor broken. On the other hand, the vitrification solution absorber of Comparative Example 1 and Comparative Example 7 did not have the ability to absorb vitrification solution and then toxicity risks to cell or tissue due to extra vitrification solution are a concern. The vitrification solution absorbers of Comparative Examples 2 to 6 have the ability to absorb vitrification solution, but deformation of the vitrification solution-absorbing layer due to swelling and shrinkage thereof was observed when cooling under liquid nitrogen after the dropping of the vitrification solution, in the course of the water absorption and the freezing of fiber of the vitrification solution-absorbing layer. Such a deformation of the vitrification solution-absorbing layer allows the cell to fall in the space between the fibers, and may cause trouble in the freezing or in the re-melting treatment at the time of thawing, or drop of the cell from the jig for vitrification preservation in a cooling vessel at the time of cryopreservation. Then, it was judged that they were not useful in practice. For the vitrification solution absorbers of Examples 1 to 11, it is understood that the adhesion of the vitrification solution-absorbing layer and the metallic support prevents the deformation of fiber and allows the preparation of the jig for vitrification cryopreservation that can withstand actual use. Furthermore, the vitrification solution absorbers of Comparative Examples 2 to 5 were difficult to handle because they could not uphold themselves in respect of the strength thereof. Note that in the vitrification solution absorbers of Examples 1 to 11, even in the case of changing the adhesion layer of polyvinyl alcohol to that of polyvinylpyrrolidone K-90 (product name), dry mass 4 g/m², manufactured by Kishida Chemical Co., Ltd., the same results as in Examples 1 to 11 were obtained for the evaluations mentioned above.

Example 12

<Preparation of Vitrification Solution Absorber>
The vitrification solution absorber of Example 12 was prepared, in the same manner as in Example 1, except for using N020F5-00F (4.0 μm in thickness, 20 g/m² in basis weight, 0.24 g/cm³ in density), a melt-blown nonwoven fabric made of nylon, manufactured by Tapyrus Co., Ltd., as a vitrification solution-absorbing layer.

Example 13

<Preparation of Vitrification Solution Absorber>
The vitrification solution absorber of Example 13 was prepared, in the same manner as in Example 1, except for using PC0070-OEM (3.5 μm in average fiber diameter, 70 g/m² in basis weight, 0.13 g/cm³ in density), a melt-blown nonwoven fabric made of hydrophilic polypropylene, manufactured by Kuraray Kuraflex Co., Ltd., as a vitrification solution-absorbing layer.

Example 14

<Preparation of Vitrification Solution Absorber>
Forty parts by mass of a stretched crystallized polyethylene terephthalate staple, fineness 0.06 dtex (fiber about 2 μm), 20 parts by mass of a stretched crystallized polyethylene terephthalate staple, fineness 0.1 dtex (fiber about 3 μm), cut length 3 mm, and 40 parts by mass of a non-stretched polyethylene terephthalate staple, fineness 0.2 dtex (fibers about 4 μm), cut length 3 mm, were wet paper-made. Then, the vitrification solution-absorbing layer, 3.0 μm in average fiber diameter, 25 g/m² in basis weight, 0.5 g/cm³ in density, was obtained by heat calendering of the surface temperature at 200° C. with adjustment of the thickness while fusing between the fibers. The vitrification solution absorber of Example 14 was prepared, in the same manner as in Example 1, except for using the above vitrification solution-absorbing layer.

Example 15

<Preparation of Vitrification Solution Absorber>
A 5% dispersion solution of cellulosic nanofiber "BinFi-s" (trade name) (0.02 μm in average fiber diameter, 2 μm in length) manufactured by Sugino Machine Ltd. was adjusted to a 2.5% dispersion solution in a water-isobutyl alcohol mixture by addition of isobutyl alcohol. Thereafter, the dispersion solution was charged into a predetermined container, and after evaporative drying, a vitrification solution-absorbing layer, 20 g/m² in basis weight, 0.4 g/cm³ in density, was obtained. The vitrification solution absorber of Example 15 was prepared, in the same manner as in Example 1, except for using the above vitrification solution-absorbing layer.

Using the vitrification solution absorbers prepared in Examples 12 to 15, evaluations were conducted, in the same manner as in Evaluations of absorbability for vitrification solution 1 and 2, and Immersion evaluation in cooling solvent mentioned above. Also, for each of the vitrification solution absorbers prepared in Examples 12 to 15, Evaluation of visibility 2 below was conducted. These results are shown in Table 2.

<Evaluation of Visibility 2>
Calcium alginate particles, about 10 μm in diameter, were prepared as a pseudo-cell. The particles were prepared in accordance with the document of "Synthesis of calcium alginate-monodispersed microspheres" (Miyazaki Prefecture Industrial laboratories) authored by Tadao Nakajima, Masataka Shimizu, and Masato Kizaki: a reference provided by SPG Techno Co., Inc., 1991, http://east.tegelog.jp/index.php?blogid=77&catid=663. First, using a 5.0 w/v % sodium alginate aqueous solution, a monodispersed W/O emulsion of which the aqueous phase was the above aqueous solution and the oil phase was n-hexane (including a 2.0 mass % sorbitan monooleate Span80 (manufactured by Wako Pure Chemical Industries, Ltd.)) was prepared by the emulsification method. In the membrane emulsification method, a connector having a hydrophobic membrane (product name: SPG pumping connector manufactured by SPG Technology Co., model number PC20U, pore size 20 μm) was used, and the aqueous phase was press-in dispersed towards the oil phase through the hydrophobic membrane to obtain the monodispersed W/O emulsion. Next, the obtained monodispersed W/O emulsion was reacted with calcium chloride to give mono-dispersion particles of calcium alginate gel. This reaction was carried out by preparing a W/O/W emulsion with press-in dispersing the monodispersed W/O emulsion towards a 10 w/v % calcium chloride aqueous solution through a hydrophilic membrane, using a connector having the hydrophilic membrane (product name SPG pumping connector manufactured by SPG Technology Co., model PC20N, pore size 20 μm), and contacting the sodium alginate aqueous solution with calcium chloride with demulsifying of the W/O/W emulsion to an O/W emulsion. The resulting calcium alginate particles were filtered off with a filter paper, and after washing with ethyl alcohol, they were dried at about 50° C. to collect the calcium alginate particles.

One of the calcium alginate particles mentioned above submerged in a vitrification solution which was prepared by mixing at the ratio of water:ethylene glycol=70:30 (to volume), was sucked together with 2 μL of the vitrification solution by micropipette, and was dropped on the vitrification solution absorbers obtained in Examples 12 to 15 (placed with the vitrification solution-absorbing layer facing upward), respectively, under observation with a reflection-type microscope (manufactured by Omron Ltd., VC4500SI microscope system). The attached pseudo-cells were observed with the reflection-type microscope mentioned above, and visibility of the cell or tissue was evaluated according to the following criteria.

◉): The pseudo-cell alone can be found after a short time, and there is such visibility that it is possible to check the shape, the size and the shading.

○): The pseudo-cell can be found after a short time, but it takes time to check the shape, the size and the shading.

x: It is not possible to check the presence of pseudo-cell, even after looking for more than one minute.

TABLE 2

|  | Evaluation of absorbability for vitrification solution 1 | Evaluation of absorbability for vitrification solution 2 | Immersion evaluation in cooling solvent | Evaluation of visibility 2 |
|---|---|---|---|---|
| Example 12 | ◉ | ◉ | ○ | ◉ |
| Example 13 | ◉ | ◉ | ○ | ◉ |
| Example 14 | ○ | ○ | ○ | ◉ |
| Example 15 | ○ | ○ | ○ | ◉ |

The vitrification solution absorbers of Examples 12 to 15 of the present invention could provide jigs for vitrification cryopreservation which were excellent in preservation of cell or tissue, in absorbability for vitrification solution, and also in visibility of cell or tissue when using a reflection-type microscope, on the grounds that the absorbers had a vitrification solution-absorbing layer containing fibers of 4 μm or less in average fiber diameter.

From the above results, it is understood that the jig for vitrification cryopreservation of the present invention is suitable for reducing the risk of toxicity due to extra vitrification solution during cryopreservation work for cell or tissue because of having an excellent ability to absorb vitrification solution. It is also understood that the jig is excellent in visibility of cell or tissue, and can reliably hold a cell or tissue even at the time of freezing or thawing.

The present invention can be used for cryopreservation of various cells or tissues such as iPS cell, ES cell, a cultured cell used popularly, a tissue for inspection or transplantation taken from a living body, and a tissue constructed in vitro in addition to using for embryo transplantation or artificial insemination of feeders such as cow and animals, and for artificial insemination to human, etc.

1 Grip portion
2 Vitrification solution absorber
2a Vitrification solution absorber
2b Vitrification solution absorber
2c Vitrification solution absorber
2d Vitrification solution absorber
2e Vitrification solution absorber
3 Vitrification solution-absorbing layer
4 Metallic support
5 Jig for vitrification cryopreservation
6 Holes structure portion
7 Adhesion layer

What is claimed is:

1. A jig for vitrification cryopreservation of cell or tissue, comprising:
   a metallic support without a hole or an internal cavity portion, wherein the metallic support is shaped in thin-plate or sheet form with a flat surface; and
   a vitrification solution absorber including an adhesion layer and a vitrification solution-absorbing layer on the metallic support in the order from the side closer to the metallic support, wherein the adhesion layer and the vitrification solution-absorbing layer are provided within the flat surface of the metallic support.

2. The jig for vitrification cryopreservation of cell or tissue according to claim 1, wherein the vitrification solution-absorbing layer is a paper or a nonwoven fabric.

3. The jig for vitrification cryopreservation of cell or tissue according to claim 2, wherein the basis weight of the vitrification solution-absorbing layer is 20 g/m$^2$ or more.

4. The jig for vitrification cryopreservation of cell or tissue according to claim 2, wherein the density of the vitrification solution-absorbing layer is 0.25 g/cm$^3$ or less.

5. The jig for vitrification cryopreservation of cell or tissue according to claim 2, wherein the density of the vitrification solution-absorbing layer is 0.5 g/cm$^3$ or less and the basis weight is 100 g/m$^2$ or less.

6. The jig for vitrification cryopreservation of cell or tissue according to claim 2, wherein the vitrification solution-absorbing layer has a fiber of 4 or less in average fiber diameter.

7. The jig for vitrification cryopreservation of cell or tissue according to claim 1, wherein the adhesion layer contains at least one of polyvinyl pyrrolidone and polyvinyl alcohol of which the degree of polymerization is 700 to 3000.

8. The jig for vitrification cryopreservation of cell or tissue according to claim 1, wherein the metallic support is 100 μm to 10 mm in thickness.

9. A method of vitrification-cryopreserving a cell or tissue, comprising the steps of:
   providing a jig for vitrification cryopreservation of cell or tissue according to claim 1;
   dropping a cell or tissue immersed in a vitrification solution together with the vitrification solution on the vitrification solution absorber of the jig;

absorbing the vitrification solution adhering around the cell or tissue in the vitrification solution-absorbing layer of the jig; and immersing the cell or tissue in liquid nitrogen while holding the cell or tissue on the vitrification solution absorber.

10. The method of vitrification-cryopreserving a cell or tissue according to claim 9, wherein the vitrification solution-absorbing layer is a paper or a nonwoven fabric.

11. The method of vitrification-cryopreserving a cell or tissue according to claim 10, wherein the basis weight of the vitrification solution-absorbing layer is 20 g/m$^2$ or more.

12. The method of vitrification-cryopreserving a cell or tissue according to claim 10, wherein the density of the vitrification solution-absorbing layer is 0.25 g/cm$^3$ or less.

13. The method of vitrification-cryopreserving a cell or tissue according to claim 10, wherein the density of the vitrification solution-absorbing layer is 0.5 g/cm$^3$ or less and the basis weight is 100 g/m$^2$ or less.

14. The method of vitrification-cryopreserving a cell or tissue according to claim 10, wherein the vitrification solution-absorbing layer has a fiber of 4 μm or less in average fiber diameter.

15. The method of vitrification-cryopreserving a cell or tissue according to claim 9, wherein the adhesion layer contains at least one of polyvinyl pyrrolidone and polyvinyl alcohol of which the degree of polymerization is 700 to 3000.

16. The method of vitrification-cryopreserving a cell or tissue according to claim 9, wherein the metallic support is 100 μm to 10 mm in thickness.

* * * * *